United States Patent
Nakamura et al.

(12) United States Patent (10) Patent No.: US 10,533,732 B2
(45) Date of Patent: Jan. 14, 2020

(54) HEADLAMP FOR HEALTHCARE WORKERS

(71) Applicants: National University Corporation Shimane University, Shimane (JP); Do Light Co., Ltd., Shimane (JP)

(72) Inventors: Morihiko Nakamura, Shimane (JP); Makie Yano, Shimane (JP); Hiroyuki Tanaka, Shimane (JP)

(73) Assignees: National University Corporation Shimane University, Shimane (JP); Do Light Co., Ltd., Shimane (JP)

( * ) Notice: Subject to any disclaimer, the term of this patent is extended or adjusted under 35 U.S.C. 154(b) by 0 days.

(21) Appl. No.: 16/069,721

(22) PCT Filed: Jan. 18, 2017

(86) PCT No.: PCT/JP2017/001442
§ 371 (c)(1),
(2) Date: Jul. 12, 2018

(87) PCT Pub. No.: WO2017/126512
PCT Pub. Date: Jul. 27, 2017

(65) Prior Publication Data
US 2019/0011116 A1 Jan. 10, 2019

(30) Foreign Application Priority Data
Jan. 20, 2016 (JP) ................................ 2016-008441

(51) Int. Cl.
*F21V 21/084* (2006.01)
*A61B 1/00* (2006.01)
(Continued)

(52) U.S. Cl.
CPC ........ *F21V 21/084* (2013.01); *A61B 1/00006* (2013.01); *A61B 1/00147* (2013.01);
(Continued)

(58) Field of Classification Search
CPC ... A61B 1/00006; A61B 1/00147; A61B 1/06; A61B 90/30; F21L 4/00; F21V 21/084;
(Continued)

(56) References Cited

U.S. PATENT DOCUMENTS 6,481,869 B1   11/2002   Horandel
6,604,847 B2 *  8/2003   Lehrer .................... F21L 14/00
                                                          362/105
(Continued)

FOREIGN PATENT DOCUMENTS

JP          3022512       3/1996
JP        2002538589     11/2002
(Continued)

OTHER PUBLICATIONS

Noda, Japan 2014-100203, Jun. 5, 2014, English Translation.*
(Continued)

*Primary Examiner* — Peggy A Neils
(74) *Attorney, Agent, or Firm* — Rankin, Hill & Clark LLP (57) ABSTRACT

A headlight (1) for a healthcare worker includes: a base part (10), which has a U-shape, is configured to come into abutment, at a center part of the base part (10), with a back side of a head and neck part of a wearer, and includes a right end part (11) and a left end part (11), each of which is configured to be hung on an upper part of an ear so that the base part (10) is retained on a head; a light source device (20), which extends from both or any one of a vicinity of the end parts (11), includes LEDs as light sources, and is configured to illuminate a region in front of the head; and a controller (30) configured to control an illumination state of the light source device (20). The controller (30) is configured to light the light source device (20) when the base part
(Continued)

(10) reaches a predetermined depression angle with a standing state of the wearer serving as a reference.

3 Claims, 8 Drawing Sheets

(51) Int. Cl.
*A61B 1/06* (2006.01)
*F21V 23/04* (2006.01)
*F21Y 115/10* (2016.01)
*F21V 7/00* (2006.01)
*F21V 7/04* (2006.01)
*F21V 23/00* (2015.01)
*F21W 131/20* (2006.01)

(52) U.S. Cl.
CPC ............ *A61B 1/06* (2013.01); *F21V 23/0485* (2013.01); *F21V 23/0492* (2013.01); *F21V 7/0066* (2013.01); *F21V 7/041* (2013.01); *F21V 7/043* (2013.01); *F21V 23/003* (2013.01); *F21W 2131/20* (2013.01); *F21Y 2115/10* (2016.08)

(58) Field of Classification Search
CPC .... F21V 23/00; F21V 23/003; F21V 23/0485; F21V 23/0492; F21V 7/0066; F21V 7/04; F21V 7/041; F21V 7/043; F21V 7/09; F21V 9/02; F21V 9/08; F21Y 2115/10; F21W 2131/20
See application file for complete search history.

(56) References Cited

U.S. PATENT DOCUMENTS

| | | | |
|---|---|---|---|
| 7,360,920 B2 | 4/2008 | Dalton | |
| 8,714,769 B2* | 5/2014 | Cristoforo | F21V 21/0816 362/191 |
| 9,096,297 B2* | 8/2015 | O'Maley | B63B 45/04 |
| 9,593,834 B2* | 3/2017 | Lee | F21V 23/0492 |
| 9,784,434 B2* | 10/2017 | Watanabe | F21V 7/06 |
| 2014/0334157 A1* | 11/2014 | Ferguson | F21V 21/084 362/277 |
| 2015/0016094 A1* | 1/2015 | Yamai | F21V 21/084 362/105 |
| 2016/0146443 A1* | 5/2016 | Steiner | F21V 23/001 362/105 |

FOREIGN PATENT DOCUMENTS

| | | |
|---|---|---|
| JP | 20143426 | 1/2014 |
| JP | 2014100203 A2 | 6/2014 |
| WO | 2005040676 A1 | 5/2005 |

OTHER PUBLICATIONS

International Search Report (ISR) dated Mar. 7, 2017 filed in PCT/JP2017/001442.
Written Opinion of the International Search Authority dated Mar. 7, 2017 filed in PCT/JP2017/001442 and its partial English translation.

* cited by examiner fig1 fig2 fig4 fig5 fig6 fig7

HEADLAMP FOR HEALTHCARE WORKERS

TECHNICAL FIELD

The present invention relates to an ear-hook type headlight for a healthcare worker, and more particularly, to a headlight for a healthcare worker with which stress given to a patient and other patients is reduced when the patient staying in a shared room is examined at night.

BACKGROUND ART

Hitherto, healthcare workers such as nurses have used a light as appropriate when observing states of patients at night.

In the simplest way, a portable light, specifically, a pen light, can be used therefor. For example, there are penlights having a clip or a strap for hanging the light that can be put into a chest pocket without being bulky, and can be taken out to illuminate a patient when required.

In addition, as disclosed in Patent Literature 1, there are also headlight-type lights with which an irradiation direction of the light can be fixed and thus an illumination state of the light can also be controlled through measurement of posture. Therefore, the headlight-type lights are highly convenient.

However, the related art has the following problems. First, there is a problem in that penlights are not always easy to handle because nurses also have medical equipment, a binder, and the like on actual site, and hence both hands are often full.

Headlights are hands-free devices, and hence do not have a problem as that of the penlights. However, headlights including the headlight disclosed in Patent Literature 1 are generally required to have in effect a flat structure with a housing having a short length in order to prevent that a head is shaken or the headlight is hit against other objects. Therefore, there is a problem in that, with the flat structure, light diffuses widely to also fall on eyes of a patient to be observed when his or her oral cavity is to be observed, for example, and hence the patient to be observed is given stress. In particular, on site, there is an opinion from other patients in the shared room that the other patients undesirably awake (are disturbed in their sleep) because the other patients perceive the light during the sleep at night. Accordingly, headlights have a problem in that patients are given stress regardless of whether the patient is the patient to be observed or not.

In addition, in Patent Literature 1, a detection angle is set to 40°, but this angle is too small in actuality when the spread of the light emitted from the headlight is also taken into consideration. That is, the headlight disclosed in Patent Literature 1 has a problem in that the detection angle cannot be considered to be a sufficient angle to prevent the other patients in the shared room from being disturbed in their sleep.

CITATION LIST

Patent Literature

[PTL 1] JP 2014-100203 A

SUMMARY OF INVENTION

Technical Problem

The present invention has been made in view of the above-mentioned problems, and it is an object of the present invention to provide a headlight for a healthcare worker that is easy to handle and hardly gives stress to patients.

Solution to Problem

According to a first aspect of the present invention, there is provided a headlight for a healthcare worker, including: a base part, which has a substantially U-shape, is configured to come into abutment, at a center part of the base part, with a back side of a head and neck part of a wearer, and includes a right end part and a left end part, each of which is configured to be hung on an upper part of an ear so that the base part is retained on the head and neck part; a light source device, which extends from both or any one of a vicinity of the right end part and a vicinity of the left end part, includes LEDs as light sources, and is configured to illuminate a region in front of a head; and a controller configured to control an illumination state of the light source device including lighting and extinguishing of the light source device, in which the controller is configured to light the light source device when the base part reaches a predetermined depression angle with a standing state of the wearer serving as a reference.

Specifically, according to a first aspect of the present invention, the light is lit when the wearer bends over to observe a state of a patient, and design flexibility including a length of a housing of the light source device is increased. As a result, it is possible to suppress diffusion of light that is more than necessary. With this, it is possible to reduce not only stress given to a patient to be observed but also stress given to other patients in a shared room especially at night. The headlight is a hands-free device, and hence is easy to handle for a nurse or another healthcare worker, too. Further, the light source device is positioned substantially at a height of eyes, and hence the line-of-sight of the wearer and an optical axis of the headlight are aligned at the same height, which gives a natural feeling of use. In addition, the headlight is a back-hanging type device, and hence the headlight does not fall on the side of the patient even if by any chance the headlight comes off the head. Also in this point, the headlight is highly convenient for medical use. With the headlight, a neck strap does not hang down when the wearer bends forward, which means workability is not impaired. Even when a separate battery is employed, a cord may be routed on the back side of the body, and hence the workability is not impaired. Moreover, LEDs are employed, and hence the headlight can be reduced in weight, and be a product having, for example, a button battery incorporated therein.

Although the depression angle depends on the spread of light, it is preferred that the depression angle have a predetermined value of 50° or more and 70° or less, and it is further preferred that the depression angle have a predetermined value of 55° or more and 65° or less.

There is no limitation on the substantially U-shape, as long as the base part can be stably retained on the back of the head by ear hooks. For example, the base part is not required to have a uniform thickness. Further, the portions of the ear hooks may have a curve to sit on the ears well. The substantially U-shape also includes a V-shape.

A proximal end of the light source device may extend as a flexible pipe separate from the right and left end parts of the base part, or may be unitary with the right and left end parts and extend together therewith. In the latter case, the right and left end parts of the base part are conceptual, but portions hanging on the ears are approximately regarded as the right and left end parts, and portions present in front of the portions of the right and left end parts are regarded as extending portions.

The controller may perform not only lighting control but also extinction control, and in addition thereto, may control change in light amount or hue of the LED. Further, when there are a plurality of LEDs, the controller may perform control of which of the plurality of LEDs are to be lighted.

The state of being hung on the upper part of the ear includes, in addition to a state of being simply put on like glasses, a state of being fit on a base of an outer ear as, for example, a frame having a D-shape.

According to a headlight for a healthcare worker of a second aspect, in the headlight for a healthcare worker of a first aspect, the light source device includes a nested structure of reflection mirrors, the LEDs include: an inner LED arranged inside an innermost reflection mirror; and an outer LED arranged between the reflection mirrors, and the controller includes a lighting mode in which only the inner LED is lit to enable provision of narrow angle light having a spread less than a spread of light exhibited when the outer LED is lit.

Specifically, according to a second aspect of the present invention, it is possible to provide the narrow angle light like a spotlight to prevent the light from entering the eyes when, for example, oral cavity observation is performed, which means switching of the light in accordance with a usage scene is enabled. Therefore, stress given to the patients can be further reduced. There may also be adopted a control mode of executing, as lighting (first lighting) performed when a predetermined depression angle is reached, a lighting mode in which only the inner LED is lit.

The housing of the reflection mirrors may have a shape of a cut prolate spheroid (ellipsoid of revolution), a cone shape, or a cylindrical shape. The housing of the reflection mirrors may have an asymmetrical shape obtained by obliquely cutting a prolate spheroid, and the side having a longer generating line may be arranged on the side apart from a face to increase light shielding property.

The nested structure does not necessarily include only the two reflection mirrors of the inner and outer reflection mirrors, and may include more reflection mirrors. In addition, the reflection mirrors are not required to be concentric or have the same shape.

The "outer LED arranged between the reflection mirrors" means, when the reflection mirrors are arranged in triplets or more, that outer LEDs are arranged between each pair of reflection mirrors.

A plurality of inner LEDs and a plurality of outer LEDs may be arranged inside the reflection mirror and between the reflection mirrors, respectively. In this case, the plurality of LEDs may be arranged not in a cluster but in a distributed manner inside the reflection mirror or between the reflection mirrors.

The narrow angle may be (about $2\pi \cdot 0.01336$ steradian in solid angle) a circle having a diameter of 7 cm to be formed at a position away from a distal end of the light source device by 30 cm, for example.

The state in which the outer LEDs are lit may be both of a state in which only the outer LEDs are lit and a state in which both of the outer LEDs and the inner LED are lit.

According to a headlight for a healthcare worker of a third aspect, in the headlight for a healthcare worker of a second aspect, the inner LED is formed of an LED configured to emit light that exits from the innermost reflection mirror with a color temperature of 5,000 K or more and 6,500 K or less, and the outer LED is formed of an LED configured to emit light that exits from between the reflection mirrors with a color temperature of 2,000 K or more and less than 5,000 K.

Specifically, according to a third aspect of the present invention, in a lighting mode in which only the inner LED is lit, a state of the patient can be appropriately observed through use of colors, for example, a complexion or a color of urine of the patient, under light having hue similar to that of white light. When the outer LEDs are lit, through use of so-called warm color light, the patients may be given less stress.

The exiting light is not necessarily limited to the light with a color temperature of the light source, but corresponds to general light (output light) including light reflected by the reflection mirrors.

According to a headlight for a healthcare worker of a fourth aspect, in the headlight for a healthcare worker of a second aspect, a gap between positions of the LEDs and a position of a distal end of a housing, in which the nested structure of reflection mirrors is housed, is formed to be relatively variable.

Specifically, according to a fourth aspect of the present invention, the position of the headlight can be adjusted so that light does not enter the eyes of the wearer. It is further possible to narrow an optical path so that the light does not excessively diffuse.

Modes of being relatively variable include: a mode in which the positions of the LEDs are not changed and the housing as a whole is moved back and forth; a mode in which the positions of the LEDs are not changed and the housing extends and contracts; and a mode in which the position of the housing is not changed and the positions of the LEDs are moved back and forth. The modes of being relatively variable also include axial rotation of the housing depending on a usage mode. A direction of the distal end of the housing corresponds to the front side (direction of visual recognition). The housing or the distal end of the housing can also be reworded as a hood or a cover.

A headlight for a healthcare worker of a fifth aspect further includes, in the headlight for a healthcare worker of a second aspect, a touch sensor, which is configured to detect contact by a finger or the like of the wearer, in which the controller is capable of switching, based on the contact detected by the touch sensor, lighting of the inner LED only and lighting of the outer LED.

Specifically, according to a fifth aspect of the present invention, lighting modes are easily switched, and hence the headlight for a healthcare worker excellent in operability can be provided.

The touch sensor may be provided on the housing of the light source device or a portion of the base part corresponding to the position of the ear, for example. Further, the touch sensor may be configured to detect a double tap and a triple tap to perform functions of changing of a light amount or extinguishing of light.

According to a headlight for a healthcare worker of a sixth aspect, in the headlight for a healthcare worker of a first aspect, the LEDs include an upper LED and a lower LED, which are arranged to be vertically aligned when the headlight is worn, the upper LED is configured to emit light having a flat shape, which exhibits a spread larger in a lateral direction than in a vertical direction, the lower LED is configured to emit light having a substantially circular shape, which exhibits a spread narrower than the spread of the upper LED exhibited in the vertical direction, and the controller includes a lighting mode in which only the upper LED is lit and a lighting mode in which only the lower LED is lit.

Specifically, according to a sixth aspect of the present invention, it is possible to provide narrow angle light like a spotlight to prevent the light from entering the eyes when, for example, oral cavity observation is performed, and in contrast, provide wide-angle light with which the whole hospital room can be surveyed, which means switching of the light in accordance with a usage scene is enabled. Therefore, stress given to the patients can be reduced. Further, the upper LED is arranged above, and provides flat wide-angle light. Accordingly, light hardly enters the eyes of the wearer. The lower LED is arranged along the line-of-sight of the wearer so that the portion to be looked at can be locally irradiated, which contributes to improving the feeling of use.

In the invention according to a sixth aspect, components and technologies of a third to fifth aspects can be employed as appropriate.

Specifically, the upper LED and the lower LED may have different color temperatures.

Further, the gap between the position of the distal end of the housing of the light source device and the positions of the LEDs can be formed to be relatively variable.

Still further, the headlight may include the touch sensor to enable the controller to switch the lighting of the lower LED and the lighting of the upper LED based on the contact detected by the touch sensor.

Advantageous Effects of Invention

According to one aspect of the present invention, a headlight for a healthcare worker that is easy to handle and hardly gives stress to patients can be provided.

DESCRIPTION OF EMBODIMENTS

First Embodiment

Now, embodiments of the present invention are described in detail with reference to the drawings. In a first embodiment of the present invention, description is given of a headlight for a healthcare worker including a LED light on its left side. In the following description, the headlight for a healthcare worker is simply referred to as "headlight" as appropriate.

Figure 1:
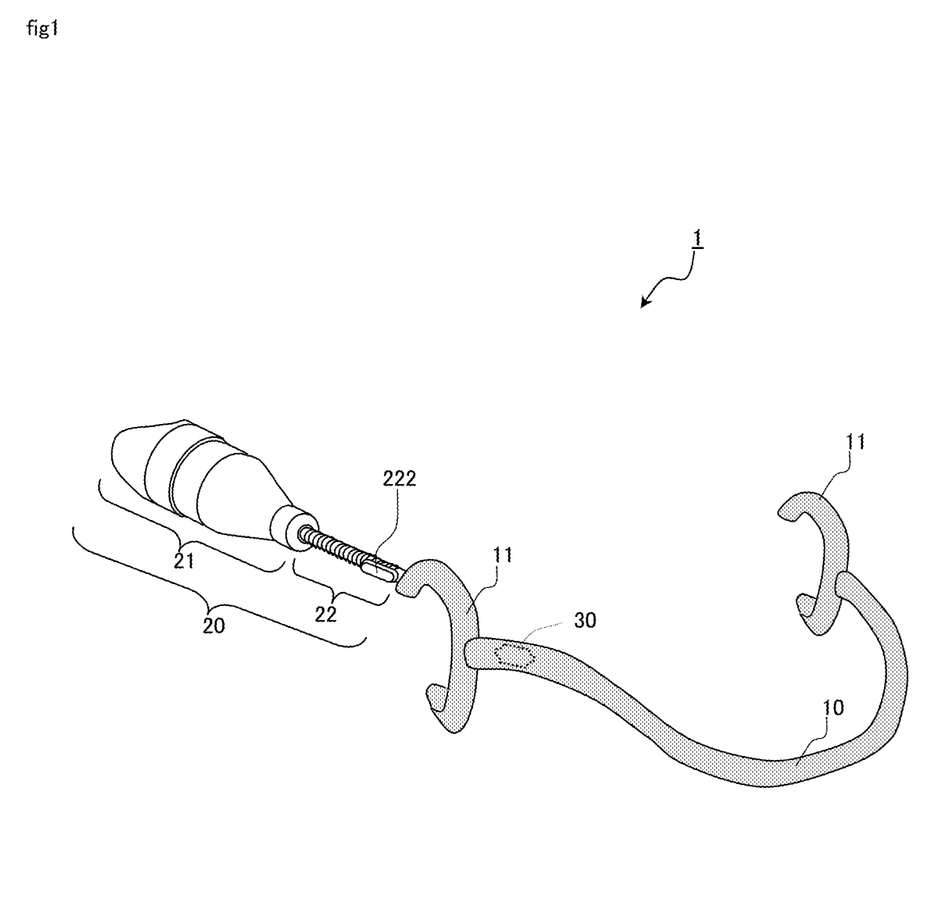
FIG. 1 is a perspective view for illustrating a headlight according to a first embodiment of the present invention.
Figure 2:
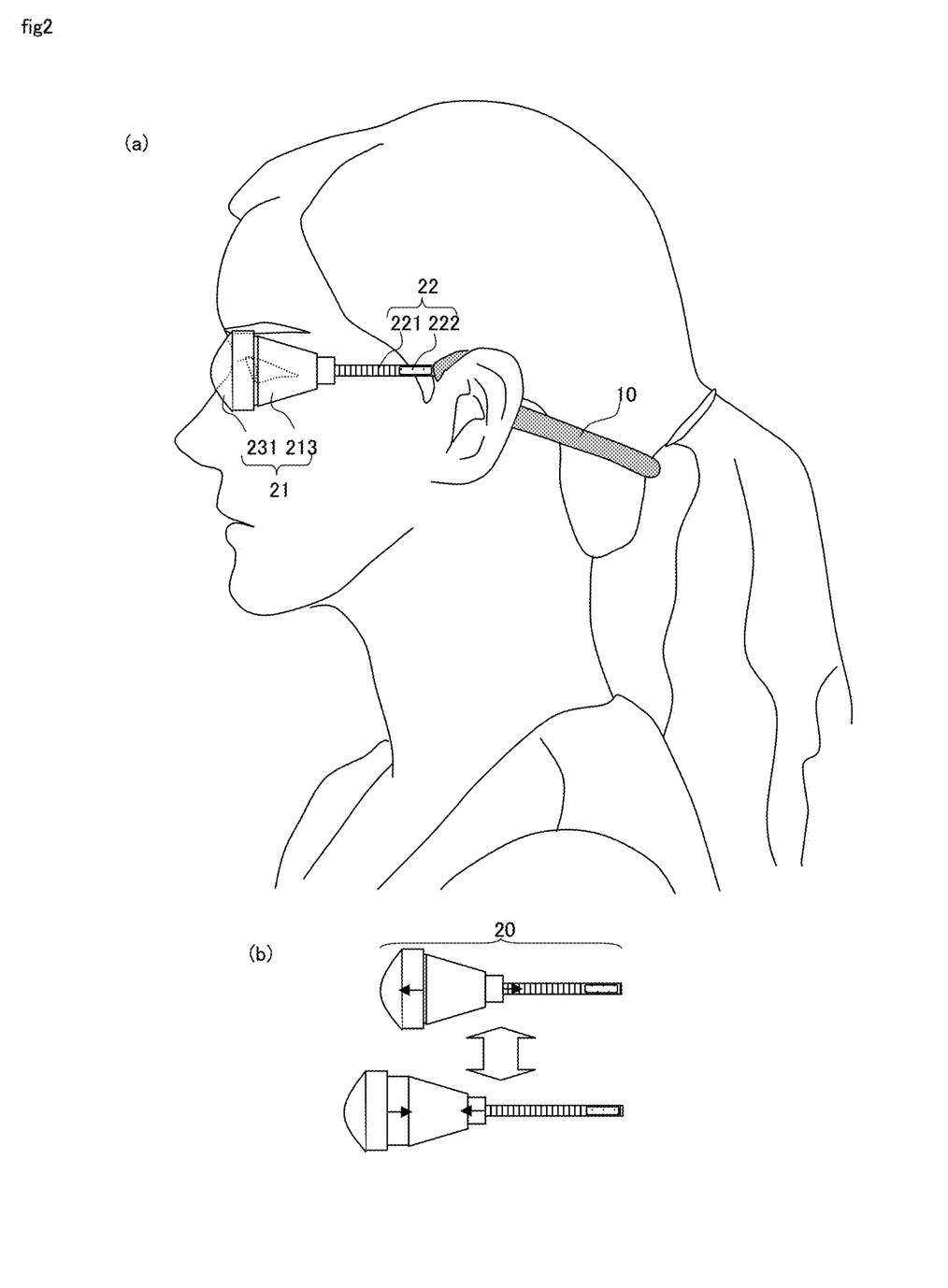
FIG. 2(a) is a schematic view for illustrating a state in which the headlight of FIG. 1 is worn.
FIG. 2(b) is an explanatory view for illustrating how a light part extends and contracts.

FIG. 1 is a perspective view of the headlight according to the first embodiment. FIG. 2(a) is a schematic view for illustrating a state in which the headlight according to the first embodiment is worn, and FIG. 2(b) is an explanatory view for illustrating how a light part extends and contracts. For the sake of convenience of description, components are omitted as appropriate in each of the drawings, and the drawings are drawn on different scales.

A headlight 1 includes a base part 10, a light source device 20, and a controller 30.

As illustrated in FIG. 1, the base part 10 has a substantially U-shape to extend along the back of a head, and has right and left end parts 11 each being formed into a C-shaped arc so as to hang on both ears well. In this manner, retention of the headlight 1 as a whole to the head is enhanced.

The material of the base part 10 is not particularly limited, but in the first embodiment, the base part 10 is formed by injection molding, and is made of plastic. The base part 10 has a skin formed by applying a thin rubber coating onto its surface. With this configuration, the one-size-fits-all headlight 1 capable of being adjusted to the shape and the size of the wearer's head is achieved, and the headlight 1 is prevented from slipping down.

Figure 3:
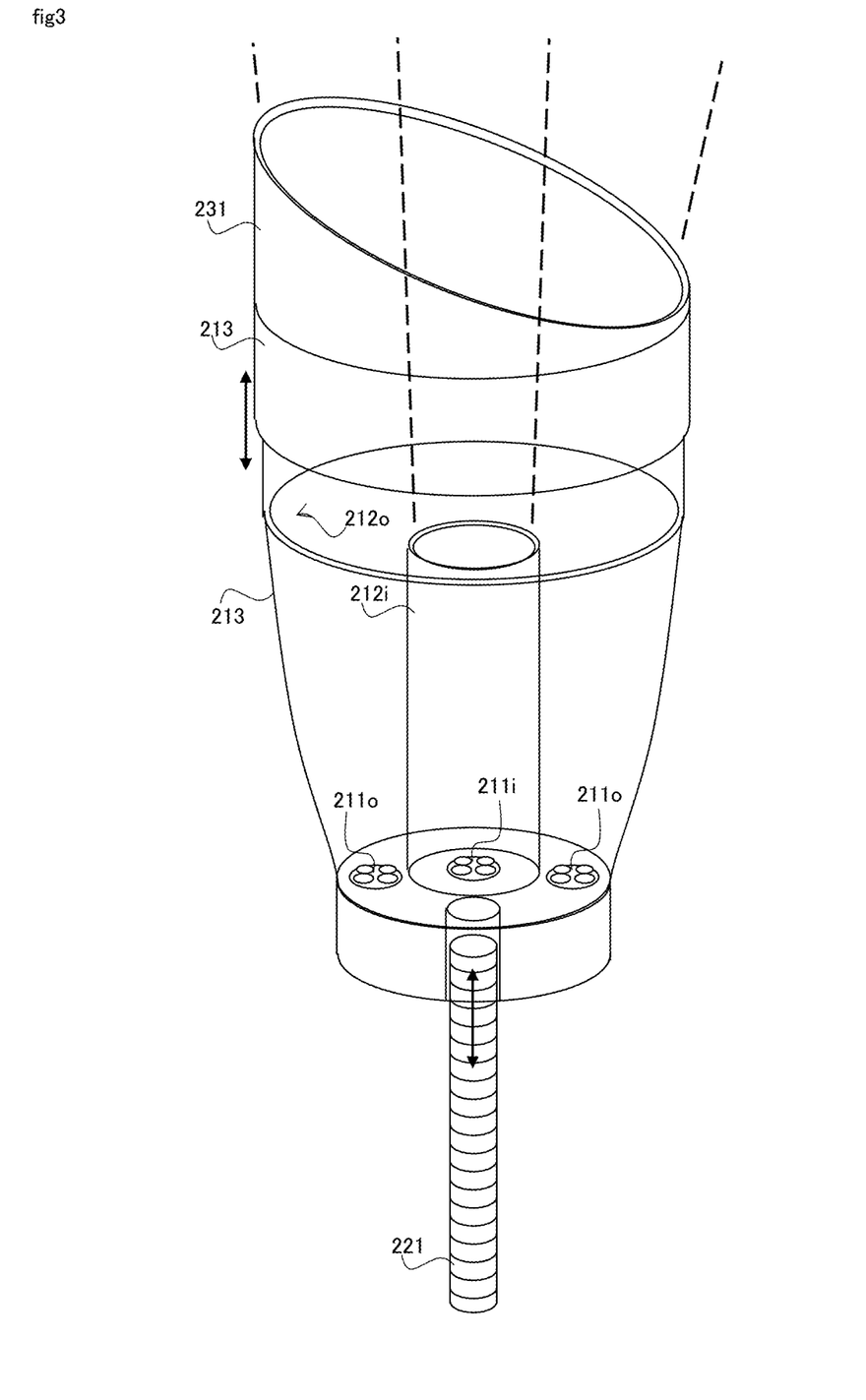
FIG. 3 is a schematic view of a light source device.

The light source device 20 includes a light part 21 and a shaft part 22. FIG. 3 is a schematic view of the light source device. In FIG. 3, for the sake of convenience of description, the light part 21 is partially seen through, and thickness thereof is also partially illustrated.

The light part 21 includes light sources 211 formed of LEDs, reflection mirrors 212, and a hood 213.

As illustrated in FIG. 3, unlike a headlight worn on a forehead, the headlight 1 can be formed long in an optical axis direction thereof. Taking advantage of this high design flexibility, the headlight 1 adopts the reflection mirrors 212 having a nested structure. Specifically, the reflection mirrors 212 include an inner reflection mirror 212i having a bottomed and substantially cylindrical shape and an outer reflection mirror 212o having a bottomed and truncated cone shape. In this case, the inner surface and the outer surface of the inner reflection mirror 212i and the inner surface of the outer reflection mirror 212o are each mirror-finished by aluminum deposition in order to prevent loss in light amount from being generated as much as possible (in order to enhance utilization efficiency of light). Therefore, a small-sized power supply can be employed to achieve the headlight with an integrated power supply (in other words, weight reduction of the headlight 1 is achieved). Depending on a specification mode, the inner side of the inner reflection mirror 212i may be mirror-finished, while the outer surface of the inner reflection mirror 212i and the inner surface of the outer reflection mirror 212o may be coated with a matte-finishing orange coating material. The reason therefor is to reduce stress given to patients through use of warm color light as described later.

The light sources 211 are formed of LEDs. An inner LED 211i is arranged on the bottom surface of the inner reflection mirror 212i, and two outer LEDs 211o are arranged on the bottom surface between the reflection mirrors 212 (portion enclosed by the outer surface of the inner reflection mirror 212i and the inner surface of the outer reflection mirror 212o).

The inner LED 211i is formed of an LED having a color temperature close to that of sunlight, and is adjusted so that light exiting from the inner reflection mirror 212i has a color temperature of 5,000 K or more and 6,500 K or less, and preferably, a color temperature of 5,000 K or more and 6,000 K or less. With this configuration, at least when only the inner LED 211i is lit, an observation target, for example, the complexion or the color of urine of a patient, can be recognized to have the same color as that observed in the daytime, which is suitable.

Meanwhile, the outer LEDs 211o are formed of LEDs having a color temperature of a warm color, for example, orange, and are adjusted so that light exiting from between the reflection mirrors 212 has a color temperature of 2,000 K or more and less than 5,000 K, and preferably, a color temperature of 2,000 K or more and 3,000 K or less. With this configuration, at least when only the outer LEDs 211o are lit, light having a so-called soft hue as light in, for example, a living room is emitted so that other patients feel less stressed even when perceiving the light.

In the headlight 1, the inner reflection mirror 212i has a long cylindrical shape, and hence light exiting therefrom travels in a substantially straight line (has a narrow spread). Meanwhile, the outer reflection mirror 212o has an enlarged diameter, and hence light exiting therefrom has a spread to some extent. In short, the reflection mirrors 212 have such a nested structure in order to enable switching between wide angle light and narrow angle light. Further, the wide angle light has a warm color, and the narrow angle light has a white color. Consequently, the headlight 1 enables different use of the light, namely, the narrow angle light like a spotlight having a high directivity is used when the complexion or the like is to be observed, whereas the wide angle light giving less stress is used when simple illumination is sufficient.

With regard to the spread of the light exiting from the inner reflection mirror 212i, it is sufficient that circular-shaped light having a diameter of from 5 cm to 9 cm be formed at a position away from the distal end of the inner reflection mirror 212i by 30 cm. In this case, the inner reflection mirror 212i is designed so that circular-shaped light having a diameter of about 6 cm is formed. This can be achieved through appropriate adjustment of the diameter and the cylinder length of the inner reflection mirror 212i and the arrangement of the inner LED 211i.

Meanwhile, the outer reflection mirror 212o is expanded to some extent, and is designed so that circular-shaped light having a diameter of from 20 cm to 60 cm is formed at a position away from the distal end of the outer reflection mirror 212o by 30 cm. This can also be achieved through appropriate adjustment of the diameter and the cylinder length of the outer reflection mirror 212o and the arrangement of the outer LEDs 211o.

In addition, the outer reflection mirror 212o is housed in the hood 213 being a housing. This hood 213 is formed of double cylindrical tubes that come into abutment with each other on a distal end side of the hood 213. The hood 213 is variable in length in an axial direction thereof by being slid (see FIG. 2(b)). With this configuration, the spread of the light exiting from the outer reflection mirror 212o can be easily adjusted on site (light is capable of being narrowed).

Further, as illustrated in FIG. 3, a flange 231 is formed on the outer surface of the distal end of the hood 213. The flange 231 is provided in order to prevent light from leaking to the outside and thereby affecting other patients. The inner surface of the hood 213 is coated with a matte-finishing black coating material so that unnecessary reflection of light is prevented.

The shaft part 22 is formed of a shaft 221 and a touch sensor 222.

The shaft 221 is formed of a flexible pipe, and is freely bent and keeps the bent posture to perform positioning of the light part 21. When the headlight 1 is actually used, the headlight 1 is hung on the ears, and is then changed in orientation by being held at the hood 213 to be positioned at a suitable position (positional relationship between and orientations of the base part 10 and the light part 21 are maintained by the shaft 221). Further, the distal end of the shaft 221 has the structure that can be pushed into and drawn out from a proximal end portion of the hood 213, and the wearer adjusts the shaft 221 to an appropriate drawn length so that it is not too bright for himself or herself (see FIG. 2(b)).

In the first embodiment, the touch sensor 222 is formed of a metal pad formed on the proximal end side of the shaft part 22 so as to have a predetermined area. A capacitive switch type is employed for the touch sensor 222 configured to detect that the wearer touches the touch sensor 222 with his or her finger. The touch sensor 222 performs control of, for example, lighting the light source device 20 in cooperation with the controller 30, which is described next.

Figure 4:
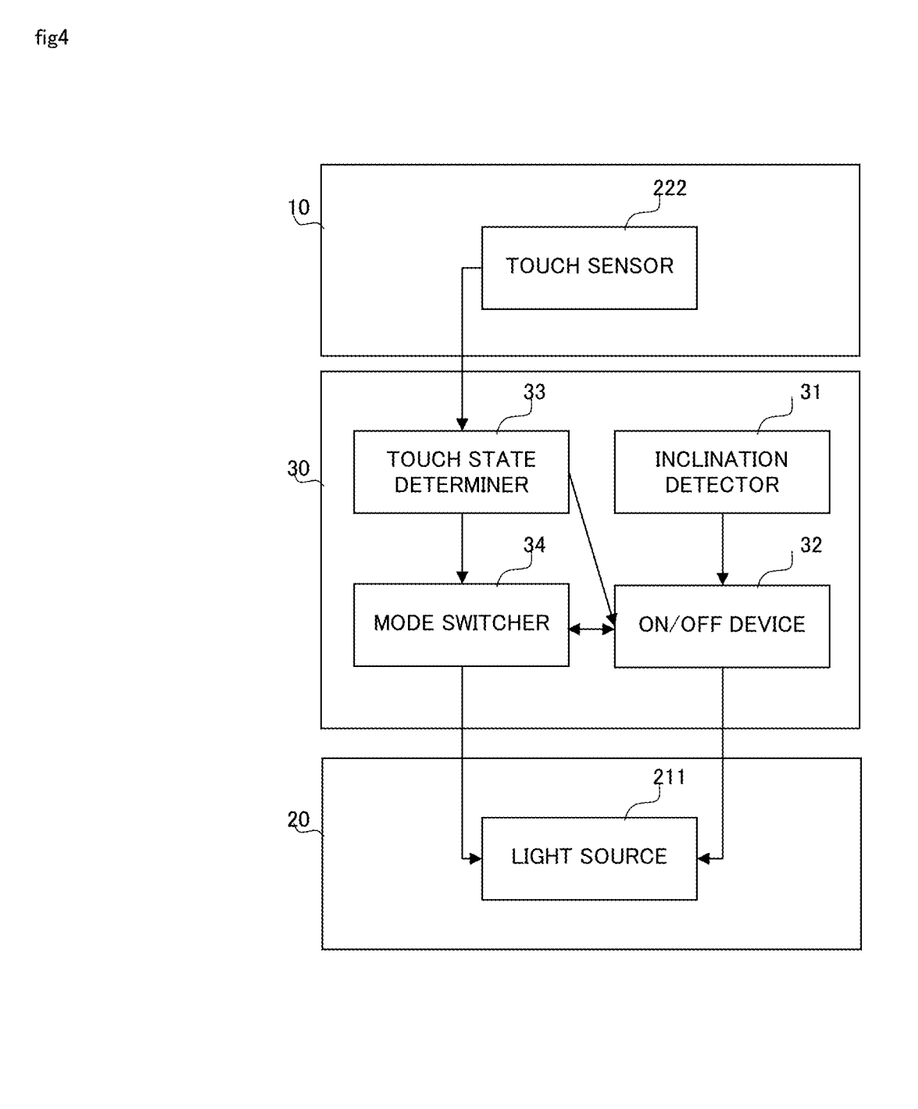
FIG. 4 is a functional block diagram of the headlight with focus on a controller.

The controller 30 is embedded in the base part 10, and performs control of an illumination state of the light part 21 including lighting and extinguishing of the light part 21, and switching of modes. FIG. 4 is a functional block diagram of the headlight 1 with focus on the controller 30. The controller 30 includes an inclination detector 31, an ON/OFF device 32, a touch state determiner 33, and a mode switcher 34.

Figure 5:
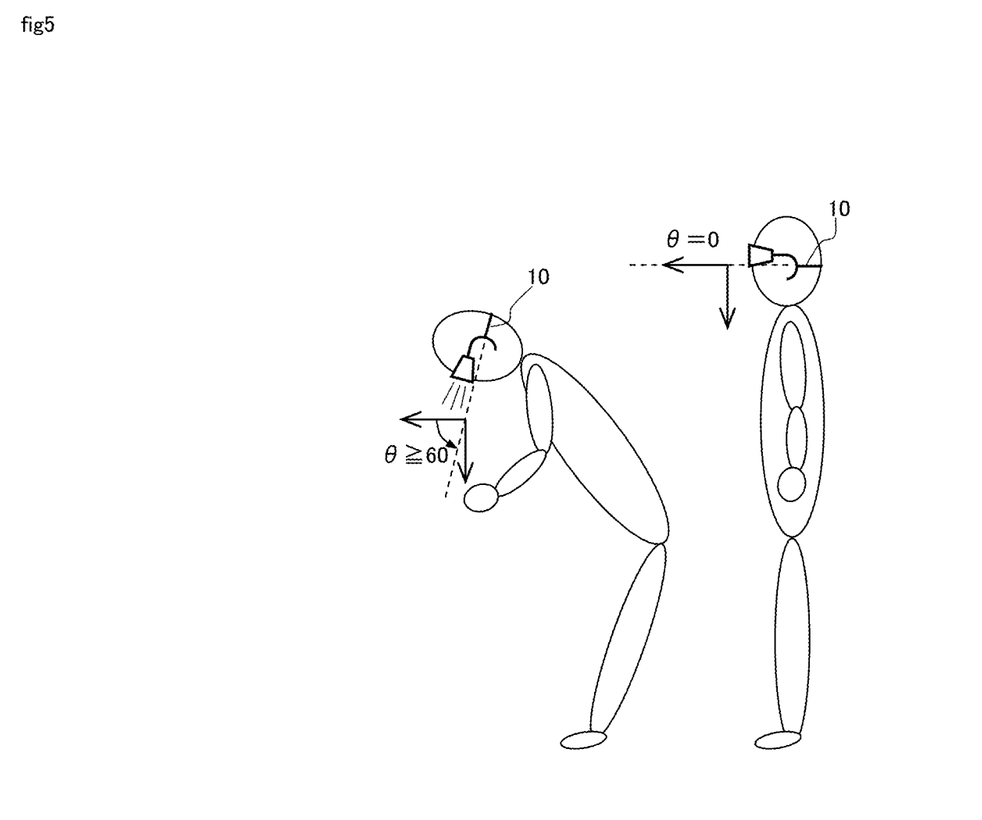
FIG. 5 is a conceptual diagram for illustrating a working posture and a depression angle.

The inclination detector 31 is formed of an acceleration sensor. Specifically, the inclination detector 31 detects, with a standing state of the wearer wearing the headlight 1 as a reference, at which angle his or her head is inclined, more specifically, at which depression angle the base part 10 is inclined. FIG. 5 is a conceptual diagram for illustrating a working posture and the depression angle. Depending on a specification mode, shaking of the head right and left may be detected so that a signal indicating the shaking of the head may be employed as a control signal for lighting or extinguishing the light part 21.

The ON/OFF device 32 controls lighting and extinguishing of the light part 21 by supplying power thereto. When the inclination detector 31 detects a depression angle of 60°, the ON/OFF device 32 lights the inner LED 211i. In actuality, when a nurse or another healthcare worker observes a patient lying on a bed, the nurse or healthcare worker bends over, and his or her head is inclined further. Therefore, in a case where the light part 21 is configured to be lit when the depression angle of 50° or more is detected, the light is prevented from being erroneously lit, with the result that the patient is prevented from being given stress.

In addition, when the touch sensor 222 detects a continuous touch for a predetermined period of time, the ON/OFF device 32 causes the inner LED 211i and the outer LEDs 211o to fade out to extinguish the inner LED 211i and the outer LEDs 211o.

In the first embodiment, power is supplied by a button battery (not shown) inserted in the base part 10. The utilization efficiency of light is enhanced through use of the reflection mirrors 212, and the light sources 211 are formed of LEDs. Accordingly, power consumption can be reduced, and a practical usage time can be secured even by a button battery. Moreover, because a button battery can be employed, the headlight 1 integrated with the power supply can be provided without being increased in weight.

Depending on a specification mode, a battery being a separate member may be put in, for example, a patch pocket of a white coat. In this case, with the headlight 1 being a so-called back-hanging type device, a cord is routed on the back side of the body. Accordingly, the cord does not hang down on the front side of the body, and hence workability is not impaired by the cord.

The touch state determiner 33 determines, based on touch information from the touch sensor 222, whether the touch is a single tap, a double tap, or a triple tap, or exhibits a state of keeping touching (continuous touch). This determination can be made by determining how many touch signals are generated within a predetermined period of time and whether electrostatic capacitance keeps changing. In the first embodiment, the single tap is not used from the point of view of prevention of erroneous operation.

The mode switcher 34 controls, based on a result of the determination made by the touch state determiner 33, a state of the light part 21 including lighting and extinguishing of the light part 21 while cooperating with the ON/OFF device 32 as appropriate. Specifically, the double tap is used for cyclic switching of lighting modes, the triple tap is used for lighting control from an extinction state, and the continuous touch is used for performing continuous or intermittent attenuation and extinction control. In this case, the cyclic switching of the lighting modes corresponds to the switching of: lighting of the inner LED 211*i* only, lighting of only one of the two outer LEDs 211*o*, lighting of the two outer LEDs 211*o*, lighting of the inner LED 211*i* and the two outer LEDs 211*o*, lighting of the inner LED 211*i* only, and so forth. Depending on a specification mode, a triple tap in a lit state may be used for extinction control.

Figure 6:
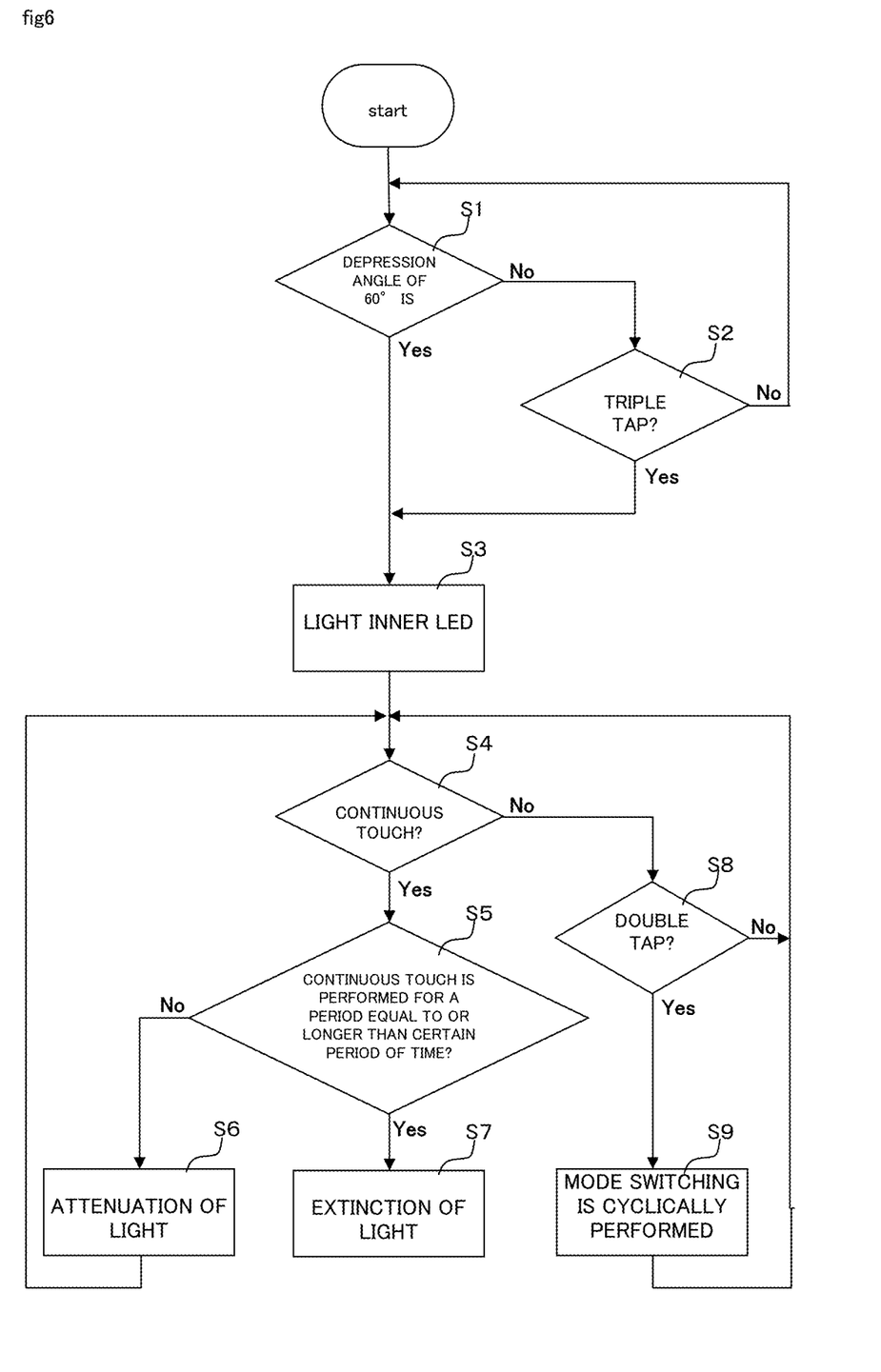
FIG. 6 is a flow chart for illustrating a control flow of the controller.

FIG. 6 is a flow chart for illustrating a control flow of the controller 30.

First, it is determined whether the depression angle of 60° is detected (Step S1). When the depression angle of 60° is not detected (Step S1: No), it is determined whether the triple tap is detected (Step S2). When the triple tap is not detected (Step S2: No), the processing returns to Step S1.

When the depression angle of 60° is detected (Step S1: Yes), or when the triple tap is performed, that is, lighting is actively required by the wearer at a time when the wearer writes in a binder numerical values or comments under a state in which the wearer stands (Step S2: Yes), only the inner LED 211*i* is lit (Step S3).

Subsequently, it is detected whether the continuous touch is performed (Step S4). When the continuous touch is performed (Step S4: Yes), it is determined whether the continuous touch is performed for a certain period of time (Step S5). When the continuous touch is performed for a period less than the certain period of time (Step S5: No), attenuation control in the current lighting mode is performed in accordance with the time period of the touch (Step S6), and then the processing returns to Step S4. When the continuous touch is performed for a period equal to or longer than the certain period of time (Step S5: Yes), the light is extinguished (Step S7).

When the continuous touch is not performed (Step S4: No), it is detected whether the double tap is performed (Step S8). When the double tap is performed (Step S8: Yes), mode switching is sequentially performed (Step S9). When the double tap is not performed (Step S8: No) or the mode switching is finished, the processing returns to Step S4.

As described above, according to the first embodiment of the present invention, it is possible to provide a headlight for a healthcare worker that is easy to handle and hardly gives stress to the patients.

The present invention is not limited to the above-mentioned configuration. For example, LED lights may be provided on both of right side and left side. Further, the touch sensor 222 may be provided on the hood 213.

In addition, in the above-mentioned example, the inner LED 211*i* is lit when the depression angle of 60° is detected or the triple tap is performed. When fade-in lighting control for gradually turning up the inner LED 211*i* is adopted, stress given to the patients can be further reduced.

Second Embodiment

In a second embodiment of the present invention, description is given of a headlight for a healthcare worker including a LED light on the right side. The same components as those of the first embodiment are denoted by the same reference symbols, and description thereof is omitted as appropriate.

Figure 7:
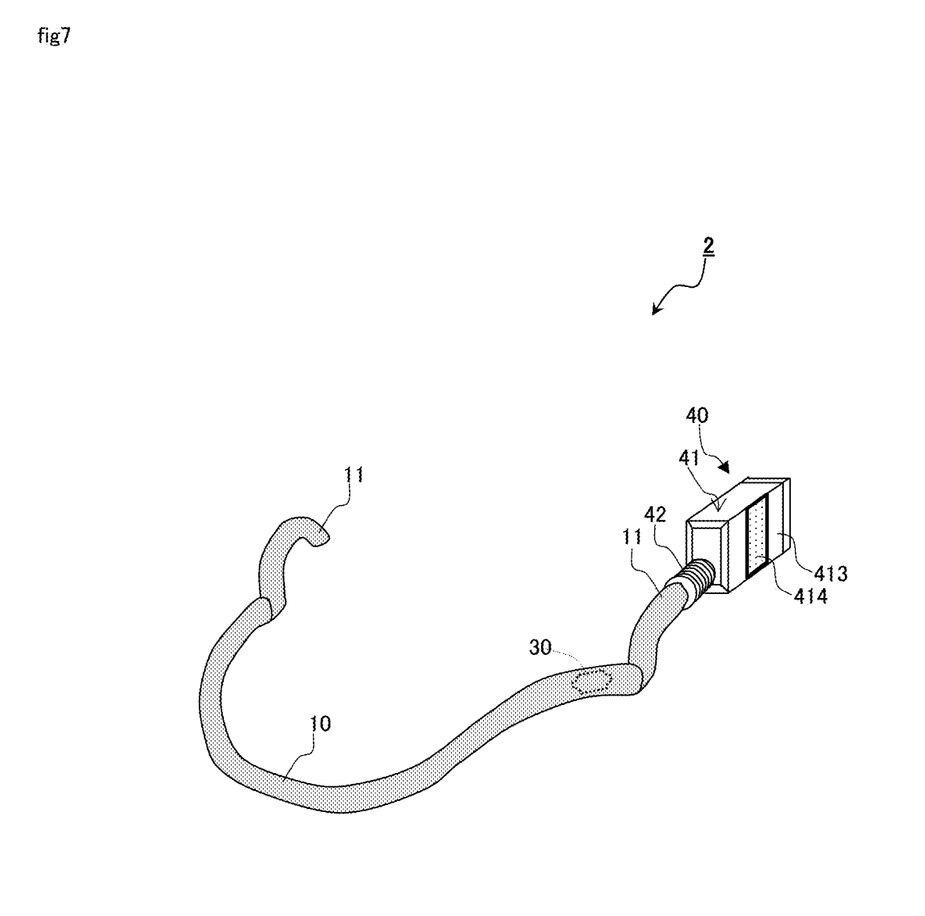
FIG. 7 is a perspective view for illustrating a headlight according to a second embodiment of the present invention.
Figure 8:
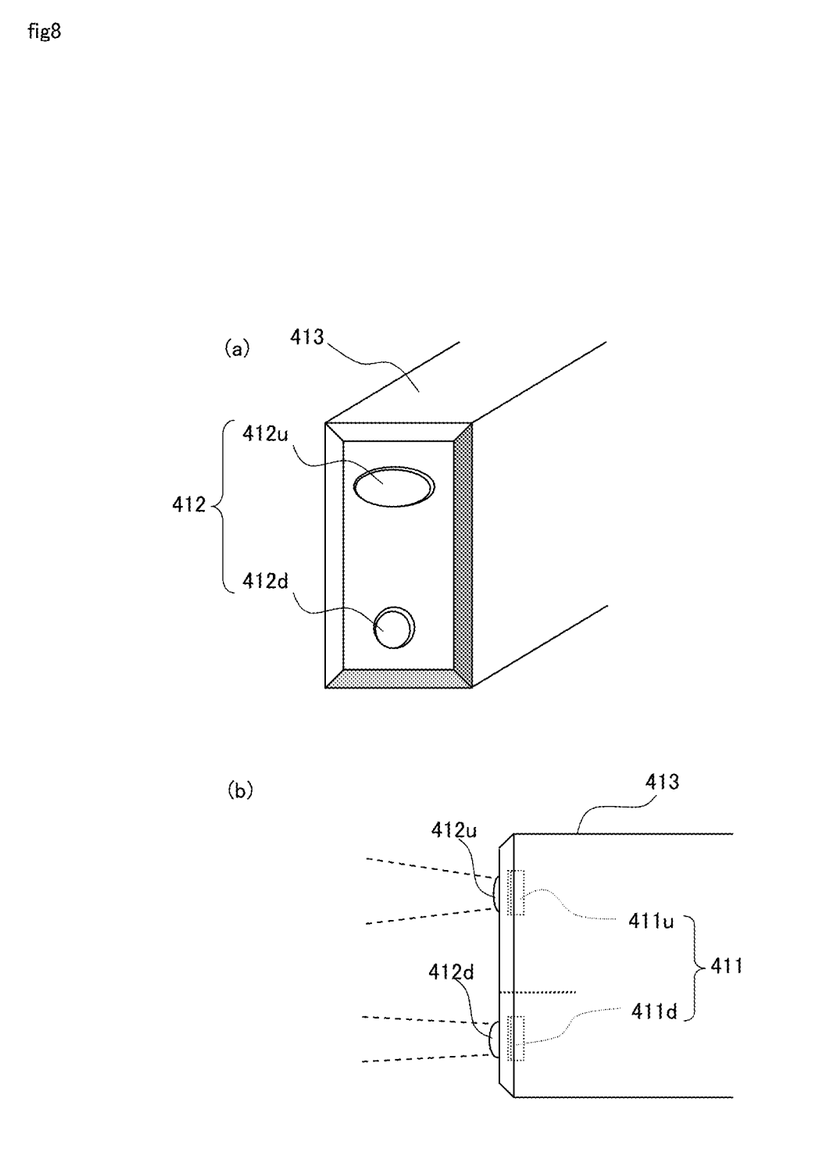
FIG. 8 are a perspective view for illustrating a front side of a light part of the headlight of FIG. 7 and a side view thereof.

FIG. 7 is a perspective view of the headlight according to the second embodiment. FIG. 8 are a perspective view (FIG. 8(*a*)) for illustrating the front side of a light source device and a side view (FIG. 8(*b*)) thereof. A headlight 2 includes a base part 10, a light source device 40, and a controller 30.

As illustrated in FIG. 7, the base part 10 has a substantially U-shape to extend along the back of the head, and has right and left end parts 11 each being formed into an arc projecting upward so as to hang on both ears well. In this manner, retention of the headlight 2 as a whole to the head is enhanced.

The light source device 40 includes a light part 41 and a shaft part 42. FIG. 8 are schematic views of the light source device. The light part 41 includes light sources 411 formed of LEDs, lenses 412, and a housing 413.

The housing 413 has a substantially rectangular parallelepiped shape, and the lenses 412 are embedded on a surface positioned in front when the headlight 2 is worn, that is, a front surface, of the housing 413. The light sources 411 are arranged behind the lenses 412.

The light sources 411 are formed of LEDs, and include an upper LED 411*u* positioned on the upper side when the headlight 2 is worn and a lower LED 411*d* positioned on the lower side when the headlight 2 is worn. The upper LED 411*u* and the lower LED 411*d* are vertically arranged in the housing 413.

In this case, the upper LED 411*u* is designed so that light is emitted via a lens 412*u* embedded on the upper side of the front surface of the housing 413 so as to have an outgoing angle of 100° (50° per side) in a rightward and leftward direction and 60° (30° per side) in an upward and downward direction and to form an elliptical shape, the color temperature of the light is from 4,000 K to 5,000 K, and the illuminance of the light obtained 3 m ahead is 2 lx.

Meanwhile, the lower LED 411*d* is designed so that circular-shaped light having a diameter of 200 mm and having a focal point 0.4 m to 0.5 m ahead of the headlight 2 forms an image by a lens 412*d* embedded on the lower side of the front surface of the housing 413, the color temperature of the light is about 3,000 K, and the illuminance of the light obtained at the focal position is 100 lx.

With regard to the spread of the light, the spread of the light emitted from the lower LED 411*d* is further narrower than the spread of the light emitted from the upper LED 411*u* in the upward and downward direction.

The upper LED 411*u* has a wide spread of the light. However, the upper LED 411*u* is arranged above eyes of the wearer, and hence it is prevented that the light directly enters the eyes or is reflected by a frame of glasses to enter the eyes. Accordingly, the headlight 2 is excellent in feeling of use. Further, the lower LED 411*d* can be positioned substantially at the height of the line-of-sight of the wearer. Accordingly, a spot is directed in a direction in which the wearer is seeing, and hence the headlight 2 is excellent in feeling of use also in this point.

The lower LED 411*d* has a lower color temperature, but the light emitted from the lower LED 411*d* has a bright warm color, and hence the lower LED 411*d* can be suitably used particularly when the complexion or the color of urine of the patient is not required to be accurately grasped.

The shaft part 42 is formed of a flexible pipe, and is freely bent and keeps the bent posture to perform positioning of the light part 41. That is, the shaft part 42 determines the posture and orientation of the housing 413. The distal end of the shaft part 42 adopts the structure that can be pushed into and drawn out from a proximal end portion of the housing 413, and the wearer adjusts the shaft part 42 to an appropriate drawn length so that it is not too bright for himself or herself.

A touch sensor 414 is formed on the side surface of the housing 413, and detects that the wearer touches the touch sensor 414 with his or her finger. The touch sensor 414 performs control of, for example, lighting the light source device 40 in cooperation with the controller 30.

The controller 30 is embedded in the base part 10, and performs control of an illumination state of the light part 41 including lighting and extinguishing of the light part 41, and switching of lighting modes. Specifically, when, with the standing state of the wearer wearing the headlight 2 serving as a reference, a depression angle of 60° is reached or a double tap on the touch sensor 414 is detected, the controller 30 lights the upper LED 411*u*. Further, when the controller 30 detects the double tap during a period in which one of the LEDs 411 is lit, the controller 30 switches the lighting of the upper LED 411*u* and the lighting of the lower LED 411*d*. Still further, when the touch sensor 414 detects a touch of 2 seconds (continuous touch), the controller 30 performs extinction control.

As described above, according to the second embodiment of the present invention, the upper LED 411*u* radiates light forming an elliptical shape (may also be a rectangular shape) whose spread is larger in the lateral direction than in the vertical direction, the lower LED 411*d* radiates light forming a substantially circular shape whose spread is narrower than the spread of the light emitted from the upper LED 411*u* in the vertical direction, and the controller 30 has a lighting mode in which only the upper LED 411*u* is lit and a lighting mode in which only the lower LED 411*d* is lit. Therefore, the headlight 2 is suitable as a headlight for a healthcare worker. In other words, it is possible to provide a headlight that is easy to handle and hardly gives stress to the patients.

Alternatively, there may be adopted a configuration in which the front surface of the housing 413 is extended forward along with the lenses 412 or leaving the lenses 412. With this configuration, the spread of the light emitted from the LEDs 411 can be adjusted.

INDUSTRIAL APPLICABILITY

The present invention is applicable not only to nursing care at night, but can also be suitably employed by an otolaryngologist or an ophthalmologist who performs a medical examination in dim light. In addition, the present invention can be utilized not only at a medical site in a narrow sense, but also at a welfare facility for the elderly, such as a retirement home, a day care facility, and a short-stay facility, as well as at a welfare facility for infants and children, such as a nursery school, a kindergarten, and a day care center.

Further, the present invention can also be utilized by a demolition worker who works at night or at a dark place. Similarly, the present invention can also be utilized by workers who work at, for example, a power company including a nuclear power plant, an ironworks, and a chemical plant, at which operation is conducted all night.

REFERENCE SIGNS LIST 1 headlight
2 headlight
10 base part
11 end part
20 light source device
21 light part
211 light source (211*i*: inner LED, 211*o*: outer LED)
212 reflection mirror (212*i*: inner reflection mirror, 212*o*: outer reflection mirror)
213 hood
22 shaft part
221 shaft
222 touch sensor
231 flange
30 controller
31 inclination detector
32 ON/OFF device
33 touch state determiner
34 mode switcher
40 light source device
41 light part
42 shaft part
411 light source (411*u*: upper LED, 411*d*: lower LED)
412 lens (412*u*: upper lens, 412*d*: lower lens)
413 housing
414 touch sensor

The invention claimed is:

1. A headlight for a healthcare worker, comprising:
a base part, which has a substantially U-shape, is configured to come into abutment, at a center part of the base part, with a back side of a head and neck part of a wearer, and includes a right end part and a left end part, each of which is configured to be hung on an upper part of an ear so that the base part is retained on the head and neck part;
a light source device, which extends from both or any one of a vicinity of the right end part and a vicinity of the left end part, includes LEDs as light sources, and is configured to illuminate a region in front of a head; and
a controller configured to control an illumination state of the light source device including lighting and extinguishing of the light source device,
wherein the controller is configured to light the light source device when the base part reaches a predetermined depression angle with a standing state of the wearer serving as a reference,
wherein the LEDs include an upper LED and a lower LED, which are arranged to be vertically aligned when the headlight is worn,
wherein the upper LED is configured to emit light having a flat shape, which exhibits a spread larger in a lateral direction than in a vertical direction,
wherein the lower LED is configured to emit light having a substantially circular shape, which exhibits a spread narrower than the spread of the upper LED exhibited in the vertical direction, and wherein the controller includes a lighting mode in which only the upper LED is lit and a lighting mode in which only the lower LED is lit.

2. The headlight for a healthcare worker according to claim 1, further comprising a touch sensor configured to detect contact by a finger or the like of the wearer,
wherein the controller is capable of switching, based on the contact detected by the touch sensor, lighting of the upper LED only and lighting of the lower LED.

3. The headlight for a healthcare worker according to claim 1,
wherein the upper LED is formed of an LED configured to emit light with a color temperature of 5,000 K or more and 6,500 K or less, and
wherein the lower LED is formed of an LED configured to emit light with a color temperature of 2,000 K or more and less than 5,000 K.

* * * * *